(12) United States Patent
Bitan

(10) Patent No.: US 12,025,446 B2
(45) Date of Patent: Jul. 2, 2024

(54) AUTOMATICALLY CREATING A TERRAIN MAPPING DATABASE

(71) Applicant: TRAILZE LTD, Tel Aviv-Jaffa (IL)

(72) Inventor: Ronen Bitan, Tel Aviv-Jaffa (IL)

(73) Assignee: TRAILZE LTD, Tel-Aviv (IL)

( * ) Notice: Subject to any disclaimer, the term of this patent is extended or adjusted under 35 U.S.C. 154(b) by 356 days.

(21) Appl. No.: 17/160,406

(22) Filed: Jan. 28, 2021

(65) Prior Publication Data

US 2021/0148708 A1    May 20, 2021

Related U.S. Application Data

(63) Continuation-in-part of application No. 16/930,376, filed on Jul. 16, 2020, now abandoned, which is a
(Continued)

(51) Int. Cl.
*G01C 21/20* (2006.01)
*A61B 5/00* (2006.01)
(Continued)

(52) U.S. Cl.
CPC ............ *G01C 21/20* (2013.01); *A61B 5/01* (2013.01); *A61B 5/021* (2013.01); *A61B 5/332* (2021.01);
(Continued)

(58) Field of Classification Search
CPC ........ G01C 21/20; G01C 21/10; G01C 21/32; G01C 21/3697; G01C 21/3804;
(Continued)

(56) References Cited

U.S. PATENT DOCUMENTS 11,193,781 B2    12/2021   Madsen et al.
2006/0155464 A1   7/2006   Smartt
(Continued)

FOREIGN PATENT DOCUMENTS

EP          2159777        3/2010
WO    WO 2008/026949       3/2008
WO    WO 2018/106763       6/2018

OTHER PUBLICATIONS

International Search Report of Application No. PCT/IL2022/050097 dated Apr. 28, 2022.
(Continued)

*Primary Examiner* — Brian P Sweeney
(74) *Attorney, Agent, or Firm* — PEARL COHEN ZEDEK LATZER BARATZ LLP

(57) ABSTRACT

Some embodiments of the present invention provide a method of navigating through a terrain using a human-scale vehicle, the method including: receiving an origin point and one or more destination points in the terrain; selecting route segments of a plurality of predefined route segments to navigate a user from the origin point to the one or more destination points in the terrain using the human-scale vehicle; obtaining motion data from one or more motion sensors disposed on at least one of the user and the human-scale vehicle during traveling of the human-scale vehicle along the selected route segments; and determining, based on at least a portion of the obtained motion data, terrain characteristics of the selected route segments.

15 Claims, 16 Drawing Sheets

Related U.S. Application Data continuation of application No. 15/698,279, filed on Sep. 7, 2017, now Pat. No. 10,718,618, which is a continuation of application No. PCT/IB2016/051305, filed on Mar. 8, 2016.

(60) Provisional application No. 62/131,314, filed on Mar. 11, 2015.

(51) Int. Cl.
| | | |
|---|---|---|
| *A61B 5/01* | (2006.01) | |
| *A61B 5/021* | (2006.01) | |
| *A61B 5/332* | (2021.01) | |
| *G01C 21/10* | (2006.01) | |
| *G01C 21/32* | (2006.01) | |
| *G01C 21/36* | (2006.01) | |
| *G01S 19/42* | (2010.01) | |
| *G01V 20/00* | (2024.01) | |
| *G06F 16/29* | (2019.01) | |
| *G09B 29/10* | (2006.01) | |

(52) U.S. Cl.
CPC ............ *A61B 5/6893* (2013.01); *G01C 21/10* (2013.01); *G01C 21/32* (2013.01); *G01C 21/3697* (2013.01); *G01S 19/42* (2013.01); *G01V 20/00* (2024.01); *G06F 16/29* (2019.01); *G09B 29/106* (2013.01)

(58) Field of Classification Search
CPC ......... G01C 21/387; A61B 5/01; A61B 5/021; A61B 5/332; A61B 5/6893; A61B 5/6801; A61B 5/6898; A61B 5/1117; A61B 5/18; G01S 19/42; G01V 99/005; G06F 16/29; G09B 29/106; G09B 29/004; G09B 29/007; G09B 29/12

See application file for complete search history.

(56) References Cited

U.S. PATENT DOCUMENTS

| | | | |
|---|---|---|---|
| 2010/0332116 | A1 | 12/2010 | Sakashita |
| 2014/0163768 | A1* | 6/2014 | Purdy .............. G08G 1/096791 701/1 |
| 2014/0303892 | A1* | 10/2014 | Morlock .............. G09B 29/007 701/533 |
| 2018/0058858 | A1 | 3/2018 | Bitan et al. |
| 2020/0124430 | A1* | 4/2020 | Bradlow ............ G06Q 30/0207 |
| 2021/0095970 | A1 | 4/2021 | Lu et al. |

OTHER PUBLICATIONS

European Search Report and Supplementary Search Report for EP Application No. 16761178.9 dated Oct. 10, 2018.
International Search Report of Application No. PCT/IB2016/051305 dated Jun. 19, 2016.
Office Action of U.S. Appl. No. 16/930,376 dated Jul. 19, 2022.
$2^{nd}$ Street, Lime; Lime Debuts Sidewalk Detection As Their Latest Innovation To Improve Scooters For All, Jan. 28, 2020.

* cited by examiner

| SEGMENTS | | |
|---|---|---|
| SEGMENT NO. | ELBOWS | CHARACTERISTICS |
| S200 | E210 | Dirt road |
| S210 | E210, E220 | Dirt road |
| S220 | E220, E230 | Gravel |
| S230 | E230, E240 | Gravel |
| S240 | E240, E250 | Dirt road |
| S250 | E250 | Dirt road |

Fig. 3A

| ELBOWS | | | |
|---|---|---|---|
| ELBOW NO. | FROM SEGMENTS | TO SEGMENT | DIRECTIVES |
| E210 | S200 | S210 | |
| E220 | S210 | S220 | |
| E230 | S220 | S230 | |
| E240 | S230 | S240 | |
| E250 | S240 | S250 | |

Fig. 3B

| SEGMENTS | | |
|---|---|---|
| SEGMENT NO. | ELBOWS | CHARACTERISTICS |
| S200 | E210 | Dirt road |
| S210 | E210, E220 | Dirt road |
| S520 | E220, E540 | Gravel |
| S530 | E540, E230 | Gravel |
| S230 | E230, E240 | Gravel |
| S240 | E240, E250 | Dirt road |
| S250 | E250 | Dirt road |

Fig. 6A

| ELBOWS |||| 
|---|---|---|---|
| ELBOW NO. | FROM SEGMENTS | TO SEGMENT | DIRECTIVES |
| E210 | S200 | S210 | |
| E220 | S210 | S520 | |
| E540 | S520 | S530 | |
| E230 | S530 | S230 | |
| E240 | S230 | S240 | |
| E250 | S240 | S250 | |

Fig. 6B

AUTOMATICALLY CREATING A TERRAIN MAPPING DATABASE

CROSS REFERENCE TO RELATED APPLICATIONS

This application is a continuation-in-part of U.S. patent application Ser. No. 16/930,376, filed on Jul. 16, 2020, which is a continuation of U.S. patent application Ser. No. 15/698,279, filed on Sep. 7, 2017, issued on Jul. 21, 2020 as U.S. Pat. No. 10,718,618, which is a continuation of International Application No. PCT/IB2016/051305, filed Mar. 8, 2016, which in turn claims the benefit of U.S. Provisional Patent Application No. 62/131,314, filed Mar. 11, 2015, all of which are incorporated by reference in their entirety herein.

FIELD OF THE INVENTION

The present invention relates to the field of navigation through a terrain and, more particularly, to navigation through a terrain using a human-scale vehicle.

BACKGROUND OF THE INVENTION

Current systems for navigating through a terrain typically treat human-scale vehicles (e.g., bicycles, scooters, etc.) either as small automotive vehicles or pedestrians.

SUMMARY OF THE INVENTION

According to an aspect of the present invention, there is provided a database for mapping off-road terrain of various characteristics in three-dimensional terms, comprising: a plurality of road segment entries, each containing data pertaining to the terrain characteristics of the segment; and a plurality of elbow entries, each containing (x, y, z) coordinates of the elbow and a record for each road segment having the elbow as one of its end points, the record comprising navigation directives for vehicles entering the segment from the elbow.

In some embodiments, each one of the road segment entries further comprises pointers to elbow entries of its end points.

In some embodiments, the navigation directives include consideration of the vehicle type.

In some embodiments, the navigation directives include consideration of the road segment that led the vehicle to the elbow.

In some embodiments, the navigation directives include 3D considerations.

In some embodiments, the navigation directives include consideration of user skills.

In some embodiments, the terrain characteristics within each the segment are substantially homogenous and are configured to be traversed using a single set of the directives.

In some embodiments, the directives are configured to be defined according to indications selected from the group consisting of: mounting slope, descending slope, sharp turn, rocky terrain, bridge over river, gravel, mud and hiking section.

In some embodiments, the indications are configured to be translated into the directives depending on the type of the vehicles.

In some embodiments, the directives are stored in the database along with references to the appropriate type of the vehicle.

In some embodiments, the terrain characteristics further comprise at least one of sand, gravel and rock.

In some embodiments, the navigation directives for the road segments are configured to be continuously derived from various sensors, cameras and microphones carried or worn by a traveler.

In some embodiments, the sensors are selected from the group consisting of: motion sensors, environmental sensors, position sensors and wearable physiological monitoring sensors.

In some embodiments, the motion sensors are selected from the group consisting of: accelerometers, gravity sensors, gyroscopes and rotational vector sensors.

In some embodiments, the environmental sensors are selected from the group consisting of: barometers, photometers and thermometers.

In some embodiments, the position sensors are selected from the group consisting of: orientation sensors, magnetometers, Global Positioning System (GPS), European Geostationary Navigation Overlay Service (EGNOS) and Global Navigation Satellite System (GLONASS).

In some embodiments, the wearable physiological monitoring sensors are configured to measure physiological parameters selected from the group consisting of: electrocardiogram (ECG), heart rate, blood pressure and body temperature.

According to another aspect of the present invention, there is provided a method of creating and continuously updating a database for mapping off-road terrain of various characteristics in three-dimensional terms, comprising: defining a plurality of road segment, each road segment defining two bounding elbows, using at least one of maps and recorded trails; for each road segment: defining preliminary terrain characteristics; for each elbow defined by the road segment: defining preliminary navigation directives for vehicles entering the segment from the elbow; and continuously updating the database using at least one of recorded trails and data from sensors carried or worn by travelers.

In some embodiments, the updating comprises updating segment definitions according to recorded trails intersecting existing segments.

In some embodiments, the updating comprises updating segment definitions according to sensors data indicating change in terrain characteristics within existing road segments.

In some embodiments, the sensors are selected from the group consisting of: motion sensors, environmental sensors, position sensors and wearable physiological monitoring sensors.

Some embodiments of the present invention may provide a method of navigating through a terrain using a human-scale vehicle, the method may include: receiving an origin point and one or more destination points in the terrain; selecting route segments of a plurality of predefined route segments to navigate a user from the origin point to the one or more destination points in the terrain using the human-scale vehicle; obtaining motion data from one or more motion sensors disposed on at least one of the user and the human-scale vehicle during traveling of the human-scale vehicle along the selected route segments; and determining, based on at least a portion of the obtained motion data, terrain characteristics of the selected route segments.

Some embodiments may include updating the selection of route segments based on the determined terrain characteristics.

Some embodiments may include updating one or more of the predefined route segments based on the terrain characteristics determined for the respective one or more selected route segments.

Some embodiments may include determining, based on at least a portion of the obtained motion data, that the human-scale vehicle has been driven on a sidewalk.

Some embodiments may include identifying locations in the terrain in which the human-scale vehicle has been driven on the sidewalk.

Some embodiments may include determining, based on at least a portion of the obtained motion data, that the human-scale vehicle has crossed a predefined 3D parking pattern bordering a parking zone within the terrain.

Some embodiments may include determining, based on geolocation data from one or more geolocation sensors disposed on at least one of the user and the human-scale vehicle that the human-scale vehicle is within the parking zone.

Some embodiments may include preventing the user from locking the human-scale vehicle if the human-scale vehicle is not within the parking zone.

Some embodiments may include determining, based on geolocation data from one or more geolocation sensors disposed on at least one of the user and the human-scale vehicle that the human-scale vehicle has left the parking zone.

Some embodiments may include preventing from the user to unlock the human-scale vehicle if the human-scale vehicle is not within the parking zone.

Some embodiments may include detecting one or more driving-related events based on at least a portion of the obtained motion data.

Some embodiments may include updating the selection of the route segments based on the one or more detected driving-related events.

Some embodiments may include updating one or more of the predefined route segments based on the one or more driving-related events detected in the respective one or more selected route segments.

Some embodiments may include at least one of selecting the route segments and updating the selection thereof based on known driving skills of the user of the human-scaled vehicle.

Some embodiments may include updating one or more of the predefined route segments based on at least a portion of the obtained motion data and based on known driving skills of the user.

Some embodiments may include generating navigation instructions based on the selected route segments.

Some embodiments may include updating the navigation instructions based on the determined terrain characteristics.

Some embodiments may include at least one of generating and updating the navigation instructions based on known driving skills of the user.

Some embodiments may include: receiving a plurality of ride datasets for the user of the human-scale vehicle, wherein each of the ride datasets may include selected route segments and motion data obtained during traveling of the human-scale vehicle along the selected route segments; and determining driving patterns for the user based on at least a portion of the ride datasets.

Some embodiments may include: receiving a plurality of ride datasets for multiple users of human-scale vehicles, wherein each of the ride datasets may include selected route segments and motion data obtained during traveling of the human-scale vehicle along the selected route segments; and at least one of defining new route segments and updating the predefined route segments based on at least a portion of the ride datasets.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same can be carried into effect, reference will now be made, purely by way of example, to the accompanying drawings in which like numerals designate corresponding elements or sections throughout.

In the accompanying drawings:

FIGS. 3A and 3B show exemplary database entries describing the partial trails of FIG. 2;

FIGS. 6A and 6B show exemplary database entries describing the segment division of FIG. 5;

Figure 1:
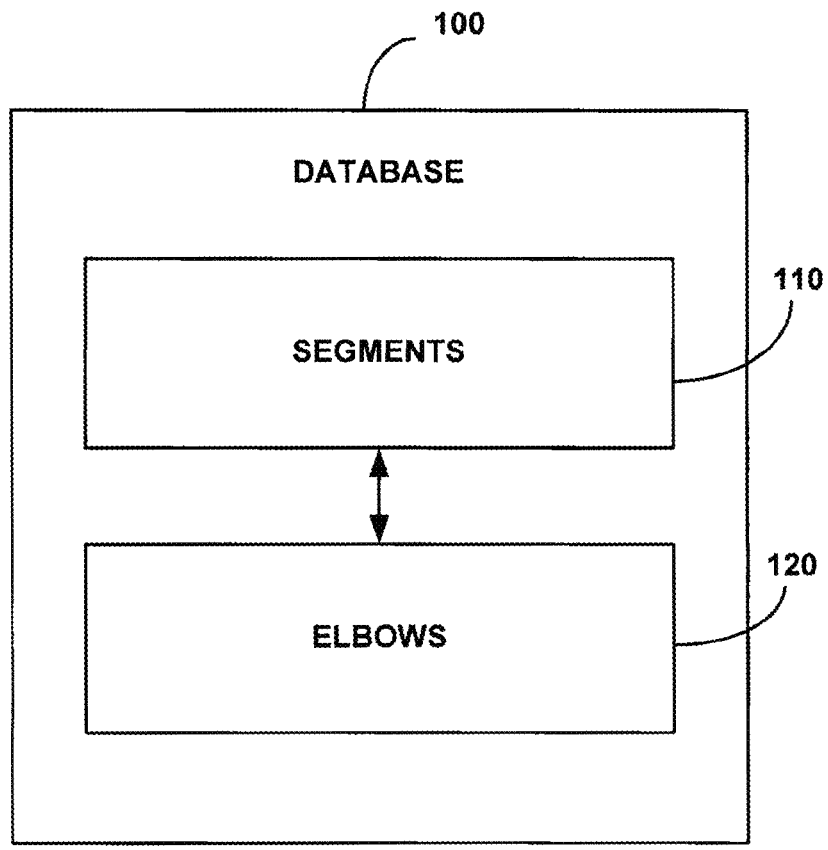
FIG. 1 is a schematic block diagram of the database according to the present invention.

It will be appreciated that, for simplicity and clarity of illustration, elements shown in the figures have not necessarily been drawn to scale. For example, the dimensions of some of the elements may be exaggerated relative to other elements for clarity. Further, where considered appropriate,

DETAILED DESCRIPTION OF THE INVENTION

In the following description, various aspects of the present invention are described. For purposes of explanation, specific configurations and details are set forth in order to provide a thorough understanding of the present invention. However, it will also be apparent to one skilled in the art that the present invention can be practiced without the specific details presented herein. Furthermore, well known features can have been omitted or simplified in order not to obscure the present invention. With specific reference to the drawings, it is stressed that the particulars shown are by way of example and for purposes of illustrative discussion of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention can be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments that can be practiced or carried out in various ways as well as to combinations of the disclosed embodiments. Also, it is to be understood that the phraseology and terminology employed herein is for the purpose of description and should not be regarded as limiting.

Unless specifically stated otherwise, as apparent from the following discussions, it is appreciated that throughout the specification discussions utilizing terms such as "processing", "computing", "calculating", "determining", "enhancing" or the like, refer to the action and/or processes of a computer or computing system, or similar electronic computing device, that manipulates and/or transforms data represented as physical, such as electronic, quantities within the computing system's registers and/or memories into other data similarly represented as physical quantities within the computing system's memories, registers or other such information storage, transmission or display devices. Any of the disclosed modules or units can be at least partially implemented by a computer processor.

The present invention provides a novel database for mapping terrain of various characteristics in three-dimensional terms. The database is constructed automatically in the system by analyzing previously recorded travelers' trails and current feedback from sensors, as will be explained in detail below.

FIG. 1 is a schematic block diagram of the database 100 according to the present invention, comprising road segments 110 and elbows 120.

Each road segment entry 110 contains data pertaining to the terrain characteristics of the segment. In a preferred embodiment of the invention, the terrain characteristics within each segment are substantially homogeneous and may be traversed using a single set of directives. Each road segment entry may also optionally point to its two bounding elbows (end points). Terrain characteristics may be, for example, sand, gravel, rock, etc.

Each elbow entry 120 includes (x, y, z) coordinates of the elbow and a record for each road segment having the elbow as one of its end points, the record including navigation directives for vehicles (or pedestrians) entering the segment from the elbow.

The directives may take into consideration:

a) The type of vehicle, if any (e.g., Car, 4WD, motorbike, bicycle, scooter, horse, pedestrian etc.)

b) The road segment that led the vehicle/user to the elbow and specifically 3D considerations, namely altitude changes between the segments.

c) The various skill levels of users in any of the vehicle types.

Figure 2:
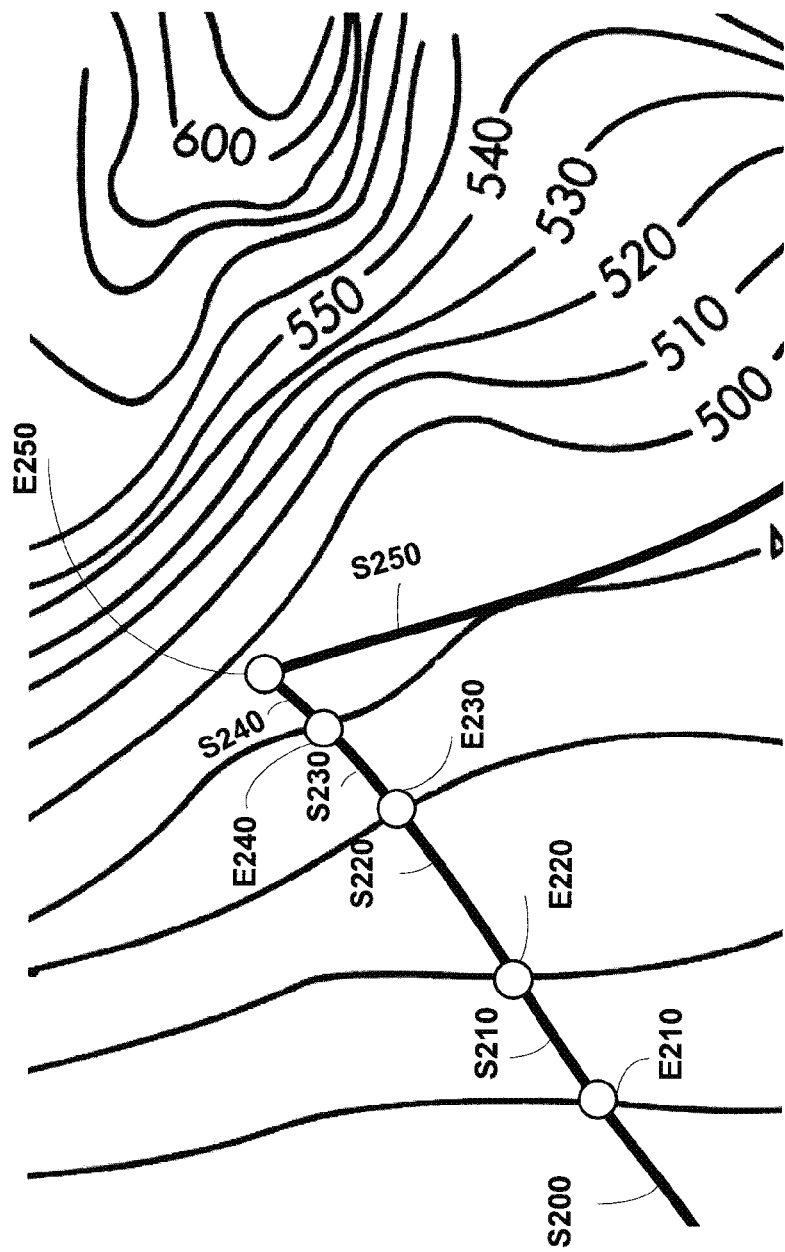
FIG. 2 is a schematic representation of a partial trails map.

FIG. 2 is a schematic representation of a partial 3D trails map described by the exemplary database entries in FIGS. 3A and 3B.

The database 100 is continuously updated, as will be explained below.

Figure 4:
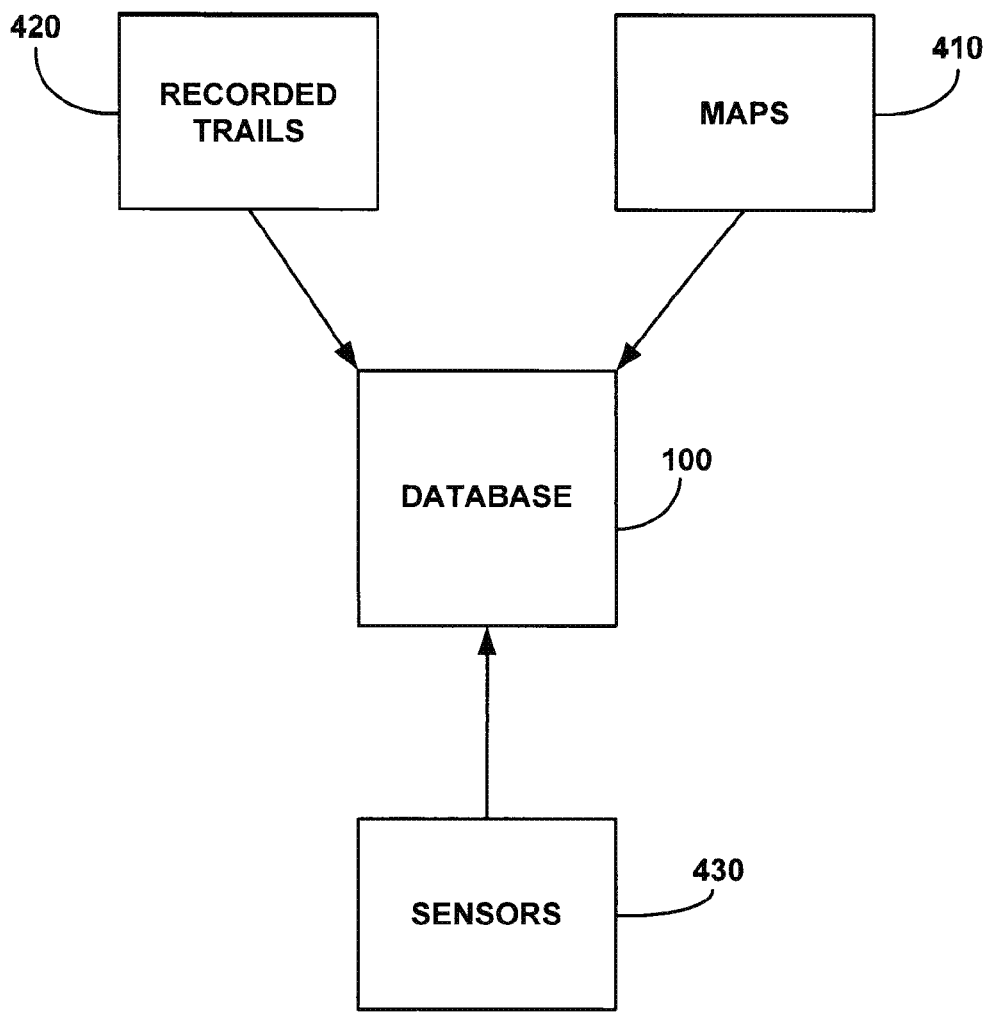
FIG. 4 is a schematic block diagram showing the various sources contributing to the creation and the on-going updating of the database.

FIG. 4 is a schematic block diagram showing the various sources contributing to the creation and the on-going updating of the database 100.

Maps 410—The basic database may be constructed using existing trails databases and/or user generated content or previously selected trails.

Existing trails databases may comprise various available Digital Elevation Models (DEM) such as the NASA DEM, or a database collected by GPS from users which are digital representations of elevations as measured at ground level. Such elevations are calculated using a variety of methods, including stereoscopy, digitized contour data, GPS data, radar signal interpretation or other methods for extracting elevation from a given position. CDEM (Canadian Digital Elevation Model) data sets for a region or a predefined area may be obtained using specific data extraction tools such as found on the web site geogratis.gc.ca.

Figure 5:
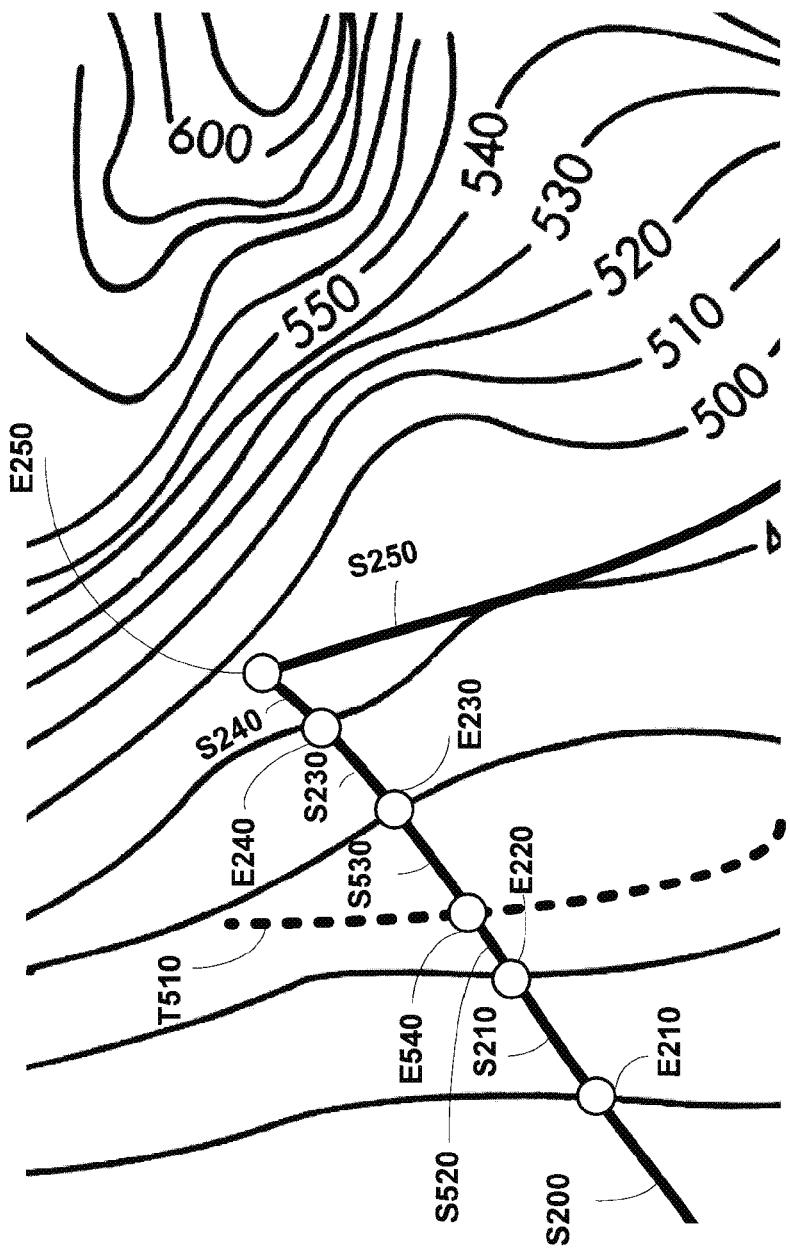
FIG. 5 shows an example of a segment being divided into two segments.

Recorded trails 420—Segments and elbows definitions may be continuously updated using recorded routes taken by travelers (e.g., by replaying captured location information). For example, if a recorded trail indicates traversing an existing segment, the segment may be divided into two segments connected by a new elbow. In the example of FIG. 5, using the partial map of FIG. 2 as a base, a new recorded trail T510 intersecting segment S220 causes the creation of a new elbow E540 which divides the previous segment S220 into two new segments S520 and S530. FIG. 6 shows the resulting updated database.

Sensors 430—Navigation directives for the various road segments may be continuously derived from various sensors carried or worn by the traveler or a vehicle, phone or additional device. The sensors may comprise, for example:

a) Motion sensors—that measure acceleration forces and rotational forces along three axes. This category includes accelerometers, gravity sensors, gyroscopes, and rotational vector sensors.

b) Environmental sensors—that measure various environmental parameters, such as ambient air temperature and pressure, illumination, and humidity. This category includes barometers, photometers, and thermometers.

c) Position sensors—that measure the physical position of a device. This category includes orientation sensors and magnetometers, Global Positioning System (GPS), European Geostationary Navigation Overlay Service (EGNOS), Global Navigation Satellite System (GLONASS), and others.

d) Wearable physiological monitoring sensors—that measure various physiological parameters of the wearer (traveler) such as, for example, electrocardiogram (ECG), heart rate, blood pressure, body temperature and others.

e) Cameras. Microphones.

The data aggregated from the various sensors is analyzed to determine terrain characteristics and levels of difficulty of trails. This computed data is then translated into directives stored in the elbows database in conjunction with the relevant segments.

The sensors data may also serve to update segments and elbows definition by identifying different characteristics in various parts of a segment, which may lead to automatically partitioning the segment into two or more segments according to the different terrain characteristics which require different directives.

Directives given to a traveler about to enter a route segment may indicate, for example, mounting slope, descending slope, sharp turn, rocky terrain, bridge over river, gravel, mud, hiking section, etc.

The various indications will be translated into different directives depending on the type of traveling vehicle. For example, "rocky terrain" may be translated into "shift to 1st gear" for a 4-wheel drive vehicle and into "walk" for a bicycle rider or initiate an alarm message such as "careful: dangerous slope ahead".

The various disrective are stored in the database along with references to the appropriate type of traveling vehicle.

Various embodiments of the present invention provide a system and a method for navigating through a terrain using a human-scale vehicle. The terrain may include, for example, an urban area and/or an area between two or more urban areas. The human-scale vehicle may be any vehicle having dimensions that enable the vehicle to drive in bicycle lanes. For example, the human-scale vehicle may be a bicycle, e-bike, scooter, electric scooter, skateboard, electric skateboards, shared bicycle, electric pedal assisted bicycle, etc.

Figure 7:
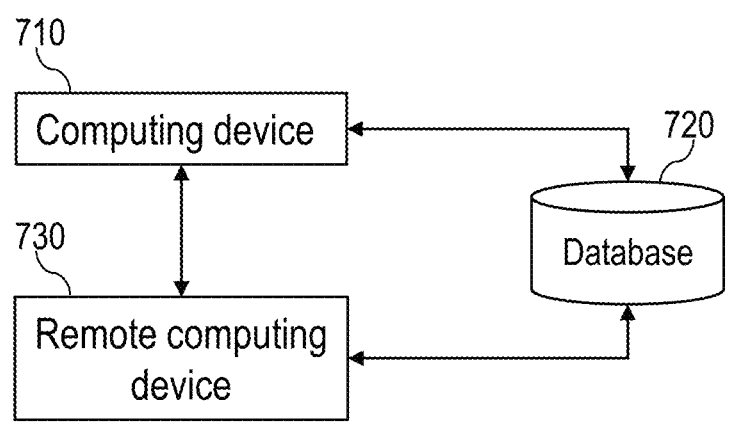
FIG. 7 is a block diagram of a system for navigating through a terrain using a human-scale vehicle, according to some embodiments of the invention.

Reference is now made to FIG. 7, which is a block diagram of a system 700 for navigating through a terrain using a human-scale vehicle, according to some embodiments of the invention.

According to some embodiments of the invention, system 700 includes a computing device 710, a database 720 and a remote computing device 730.

Computing device 710 may be, for example, a portable electronic device such as a smartphone or a tablet of a user. Computing device 710 may be, for example, an on-board computing device of the human-scale vehicle.

Computing device 710 may receive, from the user of the human-scale vehicle, an origin point and one or more destination points in the terrain.

Computing device 710 may select route segments of a plurality of predefined route segments to navigate the user from the origin point to the one or more destination points in the terrain using the human-scale vehicle. The plurality of predefined route segments may be stored in, for example, database 720.

Each of the route segments may, for example, have its unique terrain characteristics that are different from terrain characteristics of other route segments. The terrain characteristics may, for example, include a terrain type (e.g., roadway asphalt, sidewalk asphalt, pavement, etc.), a terrain condition (e.g., wet, dry, ice-crusted, bumpy, etc.), etc.

Route segments may include any section of the terrain that is suitable for driving in using the human-scale vehicle. For example, route segments may include roadway sections, pavement sections, bicycle lane sections, crosswalks, underground crossings, overhead passages, passageways, etc.

In some embodiments, two or more route segments may be associated with a single pathway section in the terrain. For example, a single pathway section in the terrain may have a roadway section, a pavement section and a bicycle lane section, e.g., parallel, or substantially parallel, to each other, wherein the roadway section, the pavement section and the bicycle lane section of the same pathway section in the terrain may be associated with different route segments.

When selecting the route segments to navigate the user from the origin point to the one or more destination points in the terrain using the human-scale vehicle, computing device 710 may prioritize the selection of those route segments that are more suitable for driving using human-scale vehicles. For example, if a particular pathway section in the terrain has a pavement section and a bicycle lane section, computing device 710 may select a route segment associated with the bicycle lane section for that particular pathway section.

In some embodiments, computing device 710 may generate navigation instructions (e.g., navigation directives) based on the selected route segments. The navigation instructions may include information concerning, for example, a maximal allowable speed along the selected route segments, turning directions at cross-roads and/or between the selected route segments, etc.

In various embodiments, computing device 710 may include a user interface or computing device 710 may be in a communication with a user interface. Computing device 710 may generate notifications indicative of the navigation instructions using the user interface. The user interface may be, for example, a display of computing device 710 (e.g., when computing device 710 is a portable electronic device such as a smartphone or a tablet of the user). The user interface may be, for example, a display of the human-scale vehicle. The user interface may include, for example, haptic guidance means (e.g., attachable to a handlebar of the human-scale vehicle). The user interface may include, for example, voice guidance means.

Computing device 710 may obtain motion data from one or more motion sensors during traveling of the human-scale vehicle along the selected route segments. The one or more motion sensors may include, for example, one or more accelerometers, one or more gyroscopes, etc. In some embodiments, the one or more motion sensors may be motion sensors of computing device 710. In some embodiments, the one or more motion sensors may be wearable by the user of the human-scale vehicle. In some embodiments, the one or more motion sensors may be disposed on the human-scale vehicle. In some embodiments, the one or more motion sensors may be motion sensors of the human-scale vehicle. For example, computing device 710 may be a portable electronic device, such as a smartphone or a tablet, having one or more motion sensors. Such computing device 710 may be attachable to the human-scale vehicle or may be wearable by the user during the driving along the selected route segments.

In some embodiments, computing device 710 may determine, based on at least a portion of the obtained motion data, terrain characteristics of the selected route segments. For example, the determined terrain characteristics may include the terrain type (e.g., roadway asphalt, bicycle lane asphalt, pavement, etc.), the terrain condition (e.g., wet, dry, ice-crusted, etc.), etc. of the selected route segments. In some embodiments, computing device 710 may transmit the obtained motion data to remote computing device 730, and remote computing device 730 may determine the terrain characteristics of the selected route segments based on at least a portion of the obtained motion data.

In some embodiments, the terrain characteristics of the selected route segments may be determined based on at least a portion of the obtained motion data and a reference motion data. For example, at least a portion of the obtained motion data may be compared to at least a portion of the reference motion data, and the terrain characteristics may be determined based on the comparison thereof. The reference motion data may be, for example, stored in database 730.

In some embodiments, the terrain characteristics of the selected route segments may be determined based on at least a portion of the obtained motion data using one or more artificial intelligence (AI) methods. For example, one or more AI methods may receive as an input at least a portion of the obtained motion data and output the terrain characteristics of the selected route segments.

In some embodiments, computing device 710 may update the selection of route segments based on the determined terrain characteristics. For example, if the terrain characteristics determined for a particular selected route segment indicate that the particular selected route segment has poor terrain conditions (e.g., wet or bumpy terrain, etc.), computing device 710 may select a different route segment of the plurality of predefined route segments having better terrain conditions than the particular selected route segment and redirect the user to the different route segment.

In some embodiments, at least one of computing device 710 and remote computing device 730 may update one or more of the predefined route segments based on the terrain characteristics determined for the respective one or more selected route segments. For example, a particular selected route segment may have a first selected route segment section having first determined terrain characteristics, and a second selected route segment section having second determined terrain characteristics. At least one of computing device 710 and remote computing device 730 may, for example, split that particular selected route segment into two new route segments, wherein a first new route segment includes the first route segment section having first determined terrain characteristics, and a second new route segment includes the second route segment section having second determined terrain characteristics. In some embodiments, the update of one or more of the predefined route segments may be performed in real-time, or substantially in real-time, based on at least a portion of the motion data being obtained by the one or more motion sensors during the actual ride along the respective one or more selected route segments.

In various embodiments, computing device 710 may generate and/or update the navigation instructions based on the determined terrain characteristics of the selected route segments. For example, if the computing device 710 determines that a particular selected route segment has poor terrain conditions (e.g., bumpy or wet terrain, etc.), computing device 710 may generate and/or update the navigation instructions so as to instruct the user of the human-scale vehicle, via the user interface, to slow down when driving along that particular selected route segment.

Figure 11:
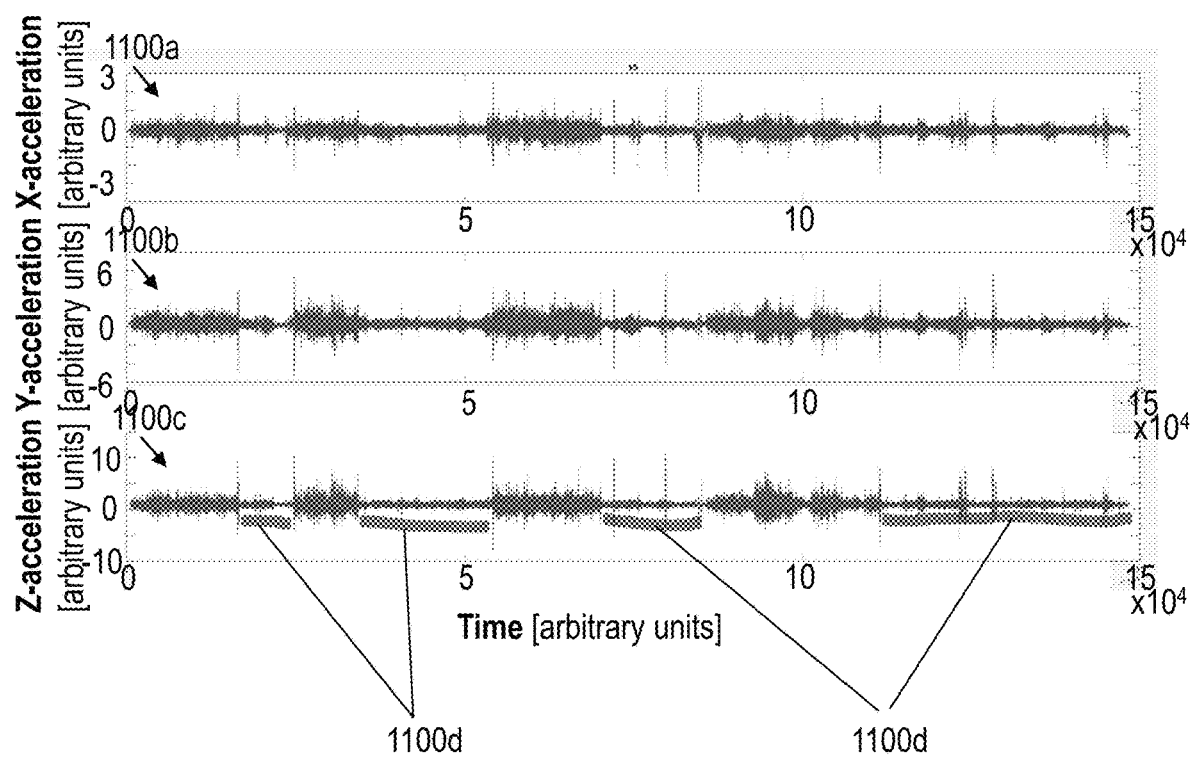
FIG. 11 shows graphs of motion data generatable by one or more motion sensors during motion of the human-scale vehicle, wherein the shown motion data is indicative of a driving on a sidewalk, according to some embodiments of the invention.

In some embodiments, at least one of computing device 710 and remote computing device 730 may determine, based on at least a portion of the obtained motion data, that the human-scale vehicle has been driven on a sidewalk (e.g., as shown in FIG. 11). In some embodiments, at least one of computing device 710 and remote computing device 730 may identify locations in the terrain in which the human-scale vehicle has been driven on the sidewalk. In some embodiments, at least one of computing device 710 and remote computing device 730 may issue a notification that the human-scale vehicle has been driven on the sidewalk. For example, the notification may be issued to the user (e.g., using the user interface, as described hereinabove) or to a third authorized party (e.g., municipal authority, etc.). Computing device 710 and/or remote computing device 730 may determine that the human-scale vehicle has been driven on the sidewalk by, for example, comparing the obtained motion data to reference motion data and/or using one or more AI methods (e.g., as described above with respect to determination of terrain characteristics).

In some embodiments, at least one of computing device 710 and remote computing device 730 may determine that the human-scale vehicle has been driven on a sidewalk further based on a geolocation data from one or more geolocation sensors (e.g., GPS sensors, etc.). The geolocation sensor(s) may be disposed on the user and/or the human-scale vehicle (e.g., as described above with respect to motion sensor(s)). For example, geolocation of the sidewalks within the terrain may be known and may be taken into account when determining that the human-scale vehicle has been driven on sidewalks.

In some cases, perimeters of parking zones for human-scale vehicles within the terrain may be bordered using a predefined three-dimensional (3D) parking pattern. In some embodiments, computing device 710 may determine, based on at least a portion of the obtained motion data, that the human-scale vehicle has crossed the predefined 3D parking pattern of a parking zone. Computing device 710 may determine that the human scale vehicle has crossed the predefined 3D parking pattern of a parking zone by, for example, comparing the obtained motion data to reference motion data and/or using one or more AI methods (e.g., as described above with respect to determination of terrain characteristics).

In some embodiments, computing device 710 may determine, based on at least a portion of the obtained motion data, that the human-scale vehicle has crossed the predefined 3D parking pattern of a parking zone, and may further determine, based on geolocation data from one or more geolocation sensors, that the human-scale vehicle is within the parking zone. In some embodiments, computing device 710 may prevent from the user to lock the human-scale vehicle if the human-scale vehicle is not within a parking zone.

In some embodiments, computing device 710 may determine, based on at least a portion of the obtained motion data, that the human-scale vehicle has crossed the predefined 3D parking pattern of a parking zone, and may further determine, based on geolocation data from one or more geolocation sensors that the human-scale vehicle has left the parking zone. In some embodiments, computing device 710 may prevent from the user to unlock the human-scale vehicle if the human-scale vehicle is not within a parking zone.

Bordering perimeters of parking zones within the terrain using predefined 3D parking patterns and determining that human-scale vehicles are within parking zones based on the obtained motion data and geolocation data may, for example, eliminate a need in installing dedicated hardware within the parking zones thereof.

In some embodiments, at least one of computing device 710 and remote computing device 730 may detect one or more driving-related events based on at least a portion of the obtained motion data. In various embodiments, the one or more driving-related events may be detected based on at least a portion of the obtained motion data, and based on the reference motion data and/or using one or more AI methods (e.g., as described hereinabove).

Figure 8:
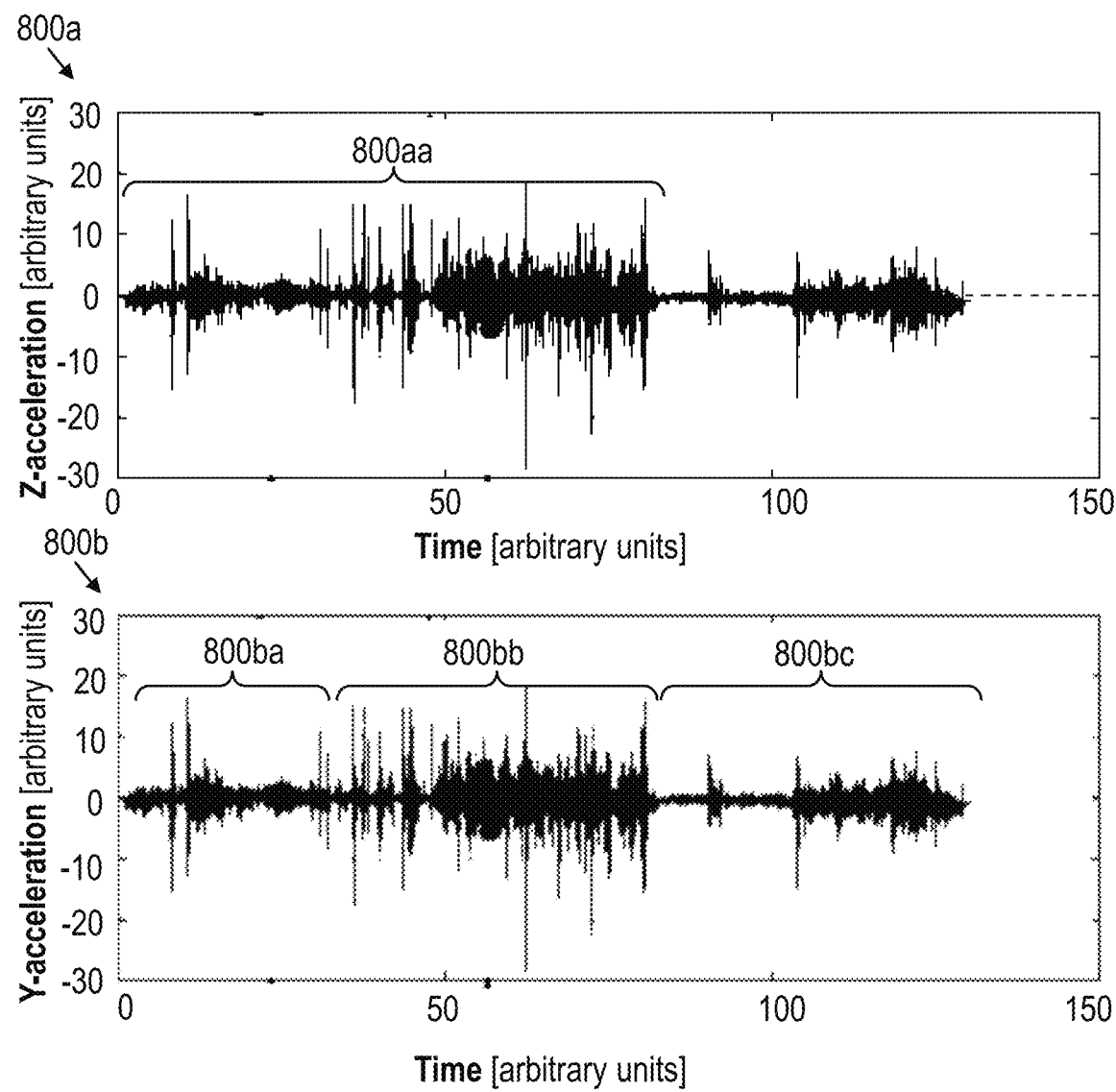
FIG. 8 shows graphs of motion data generatable by one or more motion sensors during motion of the human-scale vehicle, wherein the shown motion data is indicative of terrain characteristics and driving-related events, according to some embodiments of the invention.
Figure 9:
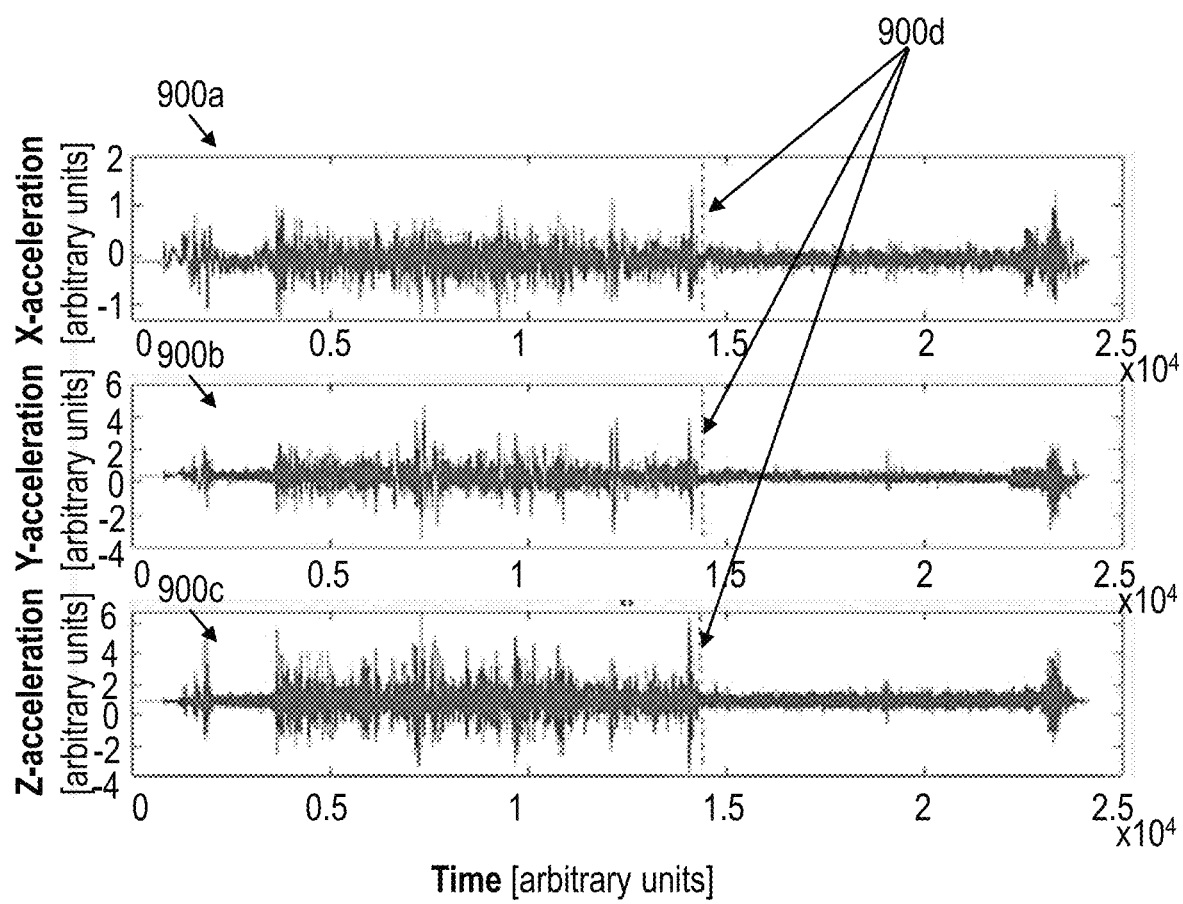
FIG. 9 shows graphs of motion data generatable by one or more motion sensors during motion of the human-scale vehicle, wherein the shown motion data is indicative of an emergency break of the human-scale vehicle, according to some embodiments of the invention.
Figure 10:
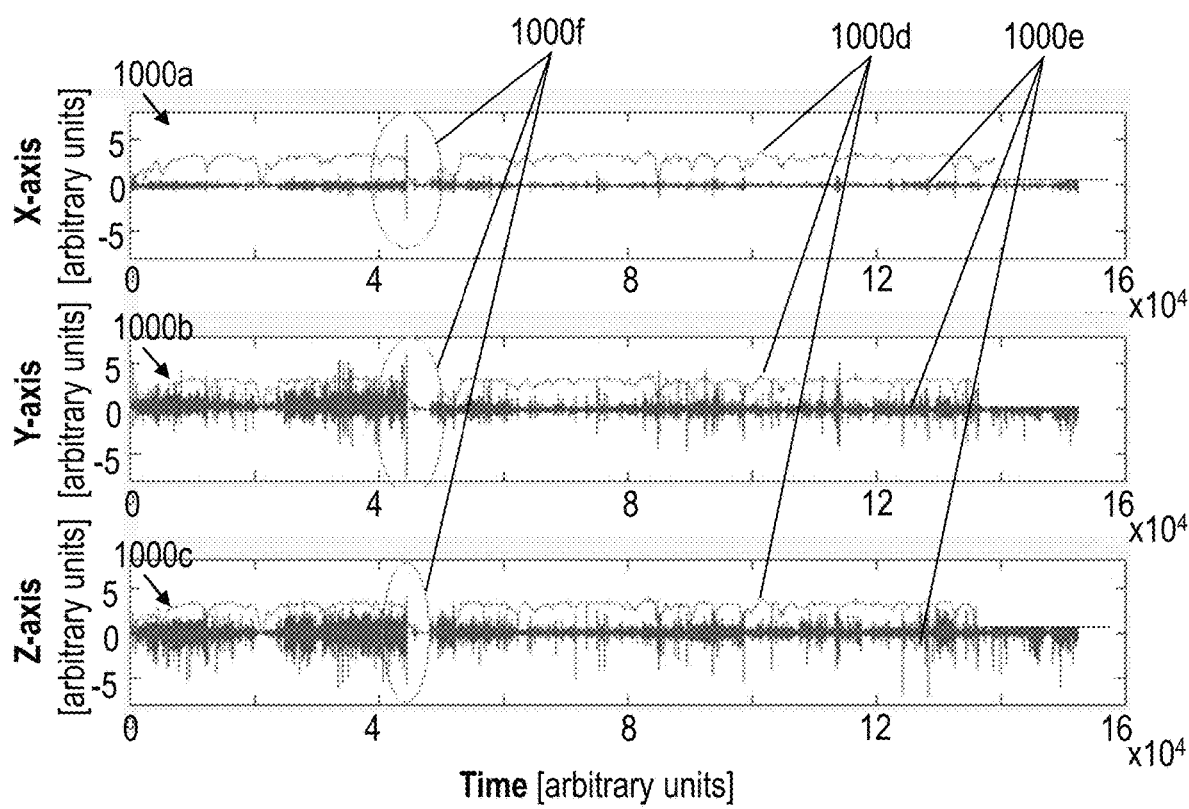
FIG. 10 shows graphs of motion data generatable by one or more motion sensors during motion of the human-scale vehicle, wherein the shown motion data is indicative of a fall of the human-scale vehicle, according to some embodiments of the invention.

The driving-related events may, for example, include an acceleration of the human-scale vehicle (e.g., as shown in FIG. 8), a deceleration of the human-scale vehicle (e.g., as shown in FIG. 8), an emergency break of the human-scale vehicle (e.g., as shown in FIG. 9), a fall of the human-scale vehicle (e.g., as shown in FIG. 10), a fall type of the human-scale vehicle (e.g., slipping, falling from a height, falling into a pit, etc.), etc.

In some embodiments, computing device 710 may update the selection of the route segments based on the one or more detected driving-related events. For example, frequent deceleration events of the human-scale vehicle may be indicative of poor terrain characteristics of a particular route segment. In this example, computing device 710 may select a different route segment of the plurality of predefined route segments and redirect the user to the different route segment.

In some embodiments, at least one of computing device 710 and remote computing device 730 may update one or more of the predefined route segments based on the one or more detected driving-related events. For example, if the user has fallen in a particular selected route segment, the predefined route segment that corresponds to that particular selected route segment may be marked as dangerous and, for example, assigned with a low priority so that this particular route has a low chance of subsequently being selected by a computing device of another user. In some embodiments, the update of the one or more of the predefined route segments is performed in real-time, or substantially in real-time, based on the one or more driving-related events detected based on at least a portion of the motion data being obtained by the one or more motion sensors during the actual ride.

In various embodiments, the selection of the route segments and/or the update of the selection thereof may be based on known driving skills of the user of the human-scaled vehicle. For example, if a particular user is skilled in driving in a terrain having known terrain characteristics (e.g., ice-crusted or wet terrain, etc.), computing device 710 may select route segments having those known terrain characteristics to navigate the user therethrough, and select other route segments for less skilled users.

In some embodiments, remote computing device 730 may update of the predefined route segments based on at least a portion of the obtained motion data and based on known driving skills of the user. For example, motion data obtained by users having high driving skills may be considered as robust data and may be used to update the predefined route segments, while motion data obtained by less skilled users may be ignored or may be marked as requiring confirmation prior to updating the predefined route segments based thereon.

In some embodiments, computing device 710 may generate and/or update the navigation instructions based on known driving skills of the user of the human-scaled vehicle. For example, if a particular user is not skilled in driving in a terrain having known terrain characteristics (e.g., ice-crusted or wet terrain, etc.), computing device 710 may instruct that user to slow down when the user drives along a route segment having those terrain characteristics.

In some embodiments, at least one of the selection of the route segments, the update of the selection of route segments, the generation of the navigation instructions and the update of the navigation instructions may be based on data from one or more geolocation sensors disposed on at least one of the human-scaled vehicle and the user thereof.

In some embodiments, at least one of the selection of the route segments, the update of the selection of route segments, the generation of the navigation instructions and the update of the navigation instructions may be based on data from one or more physiological monitoring sensors disposed on the user of the human-scaled vehicle. For example, elevated heart rate of the user may by indicative of a dangerous situation, e.g., due to an infrastructure failure, etc.

In some embodiments, at least one of the selection of the route segments, the update of the selection of route segments, the generation of the navigation instructions and the update of the navigation instructions may be based on data from one or more cameras positioned on at least one of the human-scaled vehicle and the user thereof. For example, at least one of computing device 710 and remote computing device 730 may detect and/or classify obstacles in the images from the one or more cameras (e.g., using AI methods, etc.).

In some embodiments, at least one of the selection of the route segments, the update of the selection of route segments, the generation of the navigation instructions and the update of the navigation instructions may be based on data from one or more microphones positioned on at least one of the human-scaled vehicle and the user thereof. For example, at least one of computing device 710 and remote computing device 730 may detect and/or classify obstacles based on acoustic signals from the one or more microphones (e.g., using AI methods, etc.).

In some embodiments, at least one of the selection of the route segments, the update of the selection of route segments, the generation of the navigation instructions and the update of the navigation instructions may be based on data from one or more environmental sensors positioned on at least one of the human-scaled vehicle and the user thereof.

In some embodiments, at least one of the selection of the route segments, the update of the selection of route segments, the generation of the navigation instructions and the update of the navigation instructions may be based on a type of the human-scaled vehicle. For example, different human-scale vehicle may have different driving capabilities and/or different capabilities of overcoming different obstacles (e.g., depending on the vehicle's dimensions, number of wheels, wheels type, etc.).

In some embodiments, remote computing device 730 may receive a plurality of ride datasets for multiple users of human-scale vehicles. Each of the ride datasets may include route segments that have been actually used by the users accompanied with at least one of obtained motion data, obtained geolocation data, obtained physiological data, obtained camera data, obtained microphone data, obtained environmental data and human-scale vehicle data. Remote computing device 730 may define route segments and/or or update the predefined route segments based on the plurality of the received ride datasets.

In some embodiments, remote computing device 730 may receive a plurality of ride datasets for the user of the human-scale vehicle, wherein each of the ride datasets comprises selected route segments and motion data obtained during traveling of the human-scale vehicle along the selected route segments, and may determine driving patterns for the user based on at least a portion of the ride datasets. The driving patterns determined for the user may be indicative of, for example, driving habits of the user, number of accidents the user has been involved in, the severity of those accidents, etc. The determined driving patterns may be used by, for example, one or more third parties. For example, the driving patterns determined for a user may be used by an insurance company to determine insurance quotes for the user.

Computing device 710 and remote computing device 730 may each include a non-transitory computer readable medium storing one or more subsets of instructions that, when executed, cause a processor of the respective computing device to perform functions as described hereinbelow. As would be apparent to one skilled in the art, at least some of functions described above as being performed by computing device 710 may be performed by remote computing device 730, and at least some of functions described above as being performed by remote computing device 730 may be performed by computing device 710.

Reference is now made to FIG. 8, which shows graphs 800a, 800b of motion data generatable by one or more motion sensors during motion of the human-scale vehicle, wherein the shown motion data is indicative of terrain characteristics and driving-related events, according to some embodiments of the invention.

Graphs 800a, 800b show variation with time of acceleration of the human-scale vehicle in Z-axis and Y-axis, respectively, as measured by one or more motion sensors disposed on the human-scale vehicle or on the user thereof.

Section 800aa in graph 800a may be indicative of a bumpy terrain, for example due to a "noisy" z-acceleration signal in that section.

Section 800ba in graph 800b may be indicative of an acceleration of the human-scale vehicle, for example due to a positive y-acceleration signal in that section. Section 800bb in graph 800b may be indicative of a constant velocity drive of the human-scale vehicle, for example due to a zero y-acceleration signal in that section. Section 800bc in graph 800b may be indicative of a deceleration of the human-scale vehicle, for example due to negative y-acceleration signal in that section.

Reference is now made to FIG. 9, which shows graphs 900a, 900b, 900c of motion data generatable by one or more motion sensors during motion of the human-scale vehicle, wherein the shown motion data is indicative of an emergency break of the human-scale vehicle, according to some embodiments of the invention.

Graphs 900a, 900b, 900c show variation with time of acceleration of the human-scale vehicle in X-axis, Y-axis and Z-axis, respectively, as measured by one or more motion sensors disposed on the human-scale vehicle or on the user thereof. Motion data shown in graphs 900a, 900b, 900c is indicative of an emergency break 900d of the human-scale vehicle.

Reference is now made to FIG. 10, which shows graphs 1000a, 1000b, 1000c of motion data generatable by one or more motion sensors during motion of the human-scale vehicle, wherein the shown motion data is indicative of a fall of the human-scale vehicle, according to some embodiments of the invention.

Graphs 1000a, 1000b, 1000c show variation with time of acceleration (lines 1000d) and velocity (lines 1000e) of the human-scale vehicle in X-axis, Y-axis and Z-axis, respectively, as measured by one or more motion sensors disposed on the human-scale vehicle or on the user thereof. Motion data shown in graphs 1000a, 1000b, 1000c is indicative of a fall 1000f of the human-scale vehicle.

Reference is now made to FIG. 11, which shows graphs 1100a, 1100b, 1100c of motion data generatable by one or more motion sensors during motion of the human-scale vehicle, wherein the shown motion data is indicative of a driving on a sidewalk, according to some embodiments of the invention.

Graphs 1100a, 1100b, 1100c show variation with time of acceleration of the human-scale vehicle in X-axis, Y-axis and Z-axis, respectively, as measured by one or more motion sensors disposed on the human-scale vehicle or on the user thereof. Motion data shown in graphs 1100a, 1100b, 1100c is indicative of a driving on a sidewalk (sections 1100d).

Figure 12:
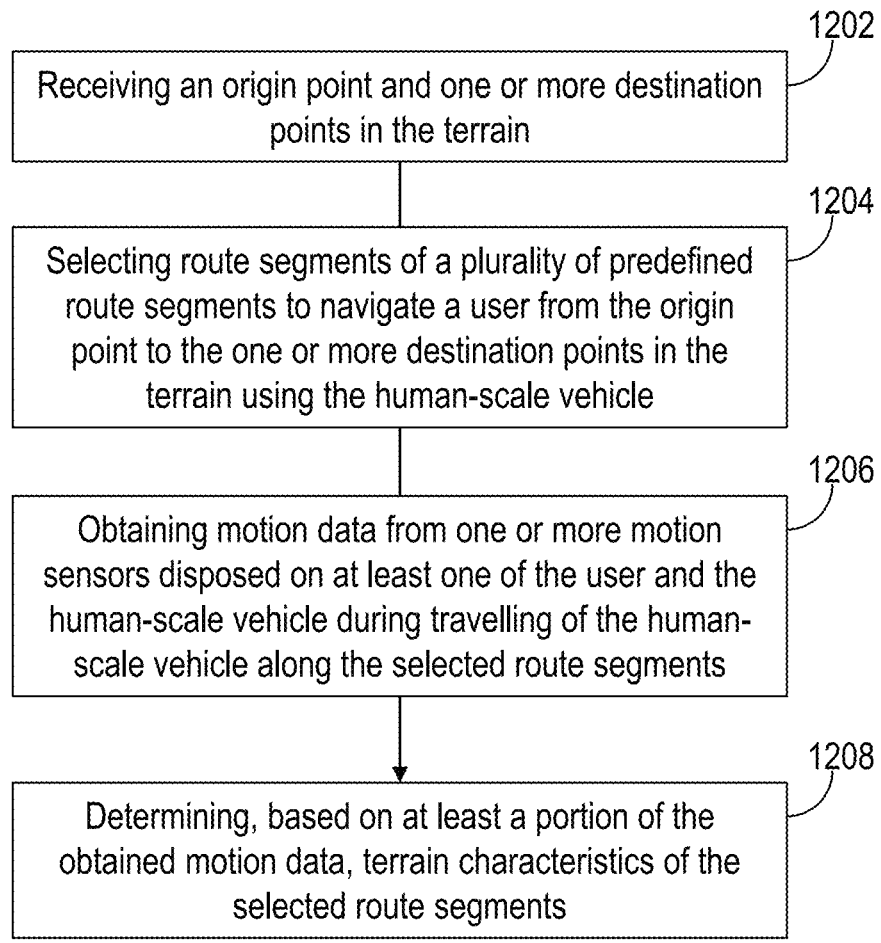
FIG. 12 is a flowchart of a method of navigating through a terrain using a human-scale vehicle, according to some embodiments of the invention.

Reference is now made to FIG. 12 which is a flowchart of a method of navigating through a terrain using a human-scale vehicle, according to some embodiments of the invention.

Some embodiments may include receiving 1202 an origin point and one or more destination points in the terrain (e.g., by computing device 710 as described above with respect to FIG. 7).

Some embodiments may include selecting 1204 route segments of a plurality of predefined route segments to navigate the user from the origin point to the one or more destination points in the terrain using the human-scale vehicle (e.g., by computing device 710 as described above with respect to FIG. 7).

Each of the route segments may, for example, have its unique terrain characteristics that are different from terrain characteristics of other route segments. The terrain characteristics may, for example, include a terrain type (e.g., roadway asphalt, sidewalk asphalt, pavement, etc.), a terrain condition (e.g., wet, dry, ice-crusted, bumpy, etc.), etc.

Route segments may include any section of the terrain that is suitable for driving in using the human-scale vehicle. For example, route segments may include roadway sections, pavement sections, bicycle lane sections, crosswalks, underground crossings, overhead passages, passageways, etc.

In some embodiments, two or more route segments may be associated with a single pathway section in the terrain. For example, a single pathway section in the terrain may have a roadway section, a pavement section and a bicycle lane section, e.g., parallel, or substantially parallel, to each other, wherein the roadway section, the pavement section and the bicycle lane section of the same pathway section in the terrain may be associated with different route segments.

When selecting the route segments to navigate the user from the origin point to the one or more destination points in the terrain using the human-scale vehicle, those route segments that are more suitable for driving using human-scale vehicles may be prioritized. For example, if a particular pathway section in the terrain has a pavement section and a bicycle lane section, a route segment associated with the bicycle lane section for that particular pathway section may be selected.

Some embodiments may include generating navigation instructions (e.g., navigation directives) based on the selected route segments (e.g., as described above with respect to FIG. 7). The navigation instructions may include information concerning, for example, a maximal allowable speed along the selected route segments, turning directions at cross-roads and/or between the selected route segments, etc.

Some embodiments may include generating notifications indicative of the navigation instructions (e.g., as described above with respect to FIG. 7).

Some embodiments may include obtaining 1206 motion data from one or more motion sensors during traveling of the human-scale vehicle along the selected route segments (e.g., as described above with respect to FIG. 7). The one or more motion sensors may include, for example, one or more accelerometers, one or more gyroscopes, etc. In some embodiments, the one or more motion sensors may be motion sensors of the computing device. In some embodiments, the one or more motion sensors may be wearable by the user of the human-scale vehicle. In some embodiments, the one or more motion sensors may be disposed on the human-scale vehicle. In some embodiments, the one or more motion sensors may be motion sensors of the human-scale vehicle.

Some embodiments may include determining 1208, based on at least a portion of the obtained motion data, terrain characteristics of the selected route segments (e.g., by computing device 710 as described above with respect to FIG. 7). For example, the determined terrain characteristics may include the terrain type (e.g., roadway asphalt, bicycle lane asphalt, pavement, etc.), the terrain condition (e.g., wet, dry, ice-crusted, etc.), etc. of the selected route segments.

In some embodiments, the terrain characteristics of the selected route segments may be determined based on at least a portion of the obtained motion data and a reference motion data. For example, at least a portion of the obtained motion data may be compared to at least a portion of the reference motion data and the terrain characteristics may be determined based on the comparison thereof.

In some embodiments, the terrain characteristics of the selected route segments may be determined based on at least a portion of the obtained motion data using one or more artificial intelligence (AI) methods. For example, one or more AI methods may receive as an input at least a portion of the obtained motion data and output the terrain characteristics of the selected route segments.

Some embodiments may include updating the selection of route segments based on the determined terrain characteristics (e.g., as described above with respect to FIG. 7). For example, if the terrain characteristics determined for a particular selected route segment indicate that the particular selected route segment has poor terrain conditions (e.g., wet or bumpy terrain, etc.), a different route segment of the plurality of predefined route segments having better terrain conditions than the particular selected route segment may be selected and the user may be redirected to the different route segment.

Some embodiments may include updating one or more of the predefined route segments based on the terrain characteristics determined for the respective one or more selected route segments (e.g., as described above with respect to FIG. 7). For example, a particular selected route segment may have a first selected route segment section having first determined terrain characteristics and a second selected route segment section having second determined terrain characteristics. That particular selected route segment may be split into two new route segments, wherein a first new route segment includes the first route segment section having first determined terrain characteristics and a second new route segment includes the second route segment section having second determined terrain characteristics. Some embodiments may include updating the one or more of the predefined route segments in real-time, or substantially in real-time, based on at least a portion of the motion data being obtained by the one or more motion sensors during the actual ride along the respective one or more selected route segments.

Various embodiments may include generating and/or updating the navigation instructions based on the determined terrain characteristics of the selected route segments (e.g., as described above with respect to FIG. 7). For example, if a particular selected route segment has poor terrain conditions (e.g., bumpy or wet terrain, etc.), the navigation instructions may be generated and/or updated so as to instruct the user of the human-scale vehicle to slow down when driving along that particular selected route segment.

Some embodiments may include determining, based on at least a portion of the obtained motion data, that the human-scale vehicle has been driven on a sidewalk (e.g., by computing device 710 and/or remote computing device 730 as described above with respect to FIGS. 7 and 11).

Some embodiments may include determining that the human-scale vehicle has been driven on the sidewalk further based on geolocation data from one or more geolocation sensors. The one or more geolocation sensors may be disposed on at least one of the user and the human-scale vehicle (e.g., as described above with respect to FIG. 7).

Some embodiments may include identifying locations in the terrain in which the human-scale vehicle has been driven on the sidewalk (e.g., as described above with respect to FIG. 7). Some embodiments may include issuing a notification that the human-scale vehicle has been driven on the sidewalk (e.g., as described above with respect to FIG. 7). For example, the notification may be issued to the user (e.g., using the user interface, as described hereinabove) or to a third authorized party (e.g., municipal authority, etc.).

In some cases, perimeters of parking zones for human-scale vehicles within the terrain may be bordered using predefined 3D parking pattern. Some embodiments may include determining, based on at least a portion of the obtained motion data, that the human-scale vehicle has crossed the predefined 3D parking pattern of a parking zone (e.g., by comparing the obtained motion data to the reference motion data and/or using one or more AI methods as described above with respect to FIG. 7).

Some embodiments may include determining, based on at least a portion of the obtained motion data, that the human-scale vehicle has crossed the predefined 3D parking pattern of a parking zone, and further determining, based on geolocation data from one or more geolocation sensors that the human-scale vehicle is within the parking zone. Some embodiments may include preventing the user from locking the human-scale vehicle if the human-scale vehicle is not within the parking zone. For example, as described above with respect to FIG. 7.

Some embodiments may include determining, based on at least a portion of the obtained motion data, that the human-scale vehicle has crossed the predefined 3D parking pattern of a parking zone, and further determining, based on geolocation data from one or more geolocation sensors, that the human-scale vehicle has left the parking zone. Some embodiments may include preventing the user from unlocking the human-scale vehicle if the human-scale vehicle is not within the parking zone. For example, as described above with respect to FIG. 7.

Some embodiments may include detecting one or more driving-related events based on at least a portion of the obtained motion data (e.g., as described above with respect to FIG. 7). In various embodiments, the one or more driving-related events may be detected based on at least a portion of the obtained motion data, and based on the reference motion data and/or using one or more AI methods (e.g., as described hereinabove).

The driving-related events may, for example, include an acceleration of the human-scale vehicle (e.g., as described above with respect to FIGS. 7 and 8), a deceleration of the human-scale vehicle (e.g., as described above with respect to FIGS. 7 and 8), an emergency break of the human-scale vehicle (e.g., as described above with respect to FIGS. 7 and 9), a fall of the human-scale vehicle (e.g., as described above with respect to FIGS. 1 and 10), a fall type of the human-scale vehicle (e.g., slipping, falling from a height, falling into a pit, etc.), etc.

Some embodiments may include updating the selection of the route segments based on the one or more detected driving-related events (e.g., as described above with respect to FIG. 7). For example, frequent deceleration events of the human-scale vehicle may be indicative of poor terrain characteristics of a particular route segment. In this example, a different route segment of the plurality of predefined route segments may be selected and the user may be redirected to the different route segment.

Some embodiments may include updating one or more of the predefined route segments based on the one or more detected driving-related events (e.g., as described above with respect to FIG. 7). For example, if the user has fallen in a particular selected route segment, the predefined route segment that corresponds to that particular selected route segment may be marked as dangerous and, for example, assigned with a low priority so as that particular route has a low chance of being selected by a computing device of another user. Some embodiments may include updating the one or more of the predefined route segments is performed in real-time, or substantially in real-time, based on the one or more driving-related events detected based on at least a portion of the motion data being obtained by the one or more motion sensors during the actual ride.

Various embodiments may include selecting the route segments and/or updating the selection thereof based on known driving skills of the user of the human-scaled vehicle (e.g., as described above with respect to FIG. 7). For example, if a particular user is skilled in driving in a terrain having known terrain characteristics (e.g., ice-crusted or wet terrain, etc.), route segments having those known terrain characteristics may be selected to navigate the user therethrough, and other route segments may be selected for less skilled users.

Some embodiments may include updating the predefined route segments based on at least a portion of the obtained motion data and based on known driving skills of the user (e.g., as described above with respect to FIG. 7). For example, motion data obtained by users having high driving skills may be considered as robust data and may be used to update the predefined route segments, while motion data obtained by less skilled users may be ignored or may be marked as requiring confirmation prior to updating the predefined route segments based thereon.

Various embodiments may include generating and/or updating the navigation instructions based on known driving skills of the user of the human-scaled vehicle (e.g., as described above with respect to FIG. 7). For example, if a particular user is not skilled in driving in a terrain having known terrain characteristics (e.g., ice-crusted or wet terrain, etc.), that user may be instructed to slow down when the user drives along a route segment having those terrain characteristics.

Some embodiments may include at least one of selecting the route segments, updating the selection of route segments, generating the navigation instructions and updating the navigation instructions based on data from one or more geolocation sensors disposed on at least one of the human-scaled vehicle and the user thereof (e.g., as described above with respect to FIG. 7).

Some embodiments may include at least one of selecting the route segments, updating the selection of route segments, generating the navigation instructions and updating the navigation instructions based on data from one or more physiological monitoring sensors disposed on the user of the human-scaled vehicle (e.g., as described above with respect to FIG. 7). For example, elevated heart rate of the user may by indicative of a dangerous situation, e.g., due to an infrastructure failure, etc.

Some embodiments may include at least one of selecting the route segments, updating the selection of route segments, generating the navigation instructions and updating the navigation instructions based on data from one or more cameras positioned on at least one of the human-scaled vehicle and the user thereof (e.g., as described above with respect to FIG. 7).

Some embodiments may include at least one of selecting the route segments, updating the selection of route segments, generating the navigation instructions and updating the navigation instructions based on data from one or more microphones positioned on at least one of the human-scaled vehicle and the user thereof (e.g., as described above with respect to FIG. 7).

Some embodiments may include at least one of selecting the route segments, updating the selection of route segments, generating the navigation instructions and updating the navigation instructions based on data from one or more environmental sensors positioned on at least one of the human-scaled vehicle and the user thereof (e.g., as described above with respect to FIG. 7).

Some embodiments may include at least one of selecting the route segments, updating the selection of route segments, generating the navigation instructions and updating the navigation instructions based on a type of the human-scaled vehicle (e.g., as described above with respect to FIG. 7).

Some embodiments may include receiving a plurality of ride datasets for multiple users of human-scale vehicles (e.g., as described above with respect to FIG. 7). Each of the ride datasets may include route segments that have been actually used by the users accompanied with at least one of obtained motion data, obtained geolocation data, obtained physiological data, obtained camera data, obtained microphone data, obtained environmental data and human-scale vehicle data. Various embodiments may include defining route segments and/or or updating the predefined route segments based on the plurality of the received ride datasets.

Some embodiments may include receiving a plurality of ride datasets for the user of the human-scale vehicle, each of the ride datasets comprises selected route segments and motion data obtained during traveling of the human-scale vehicle along the selected route segments, and determining driving patterns for the user based on at least a portion of the ride datasets (e.g., as described above with respect to FIG. 7). The driving patterns determined for the user may be indicative of, for example, driving habits of the user, number of accidents the user has been involved in, the severity of the accidents thereof, etc. The determined driving patterns may be used by, for example, one or more third parties. For example, the driving patterns determined for a user may be used by an insurance company to determine insurance quotes for the user.

Figure 13:
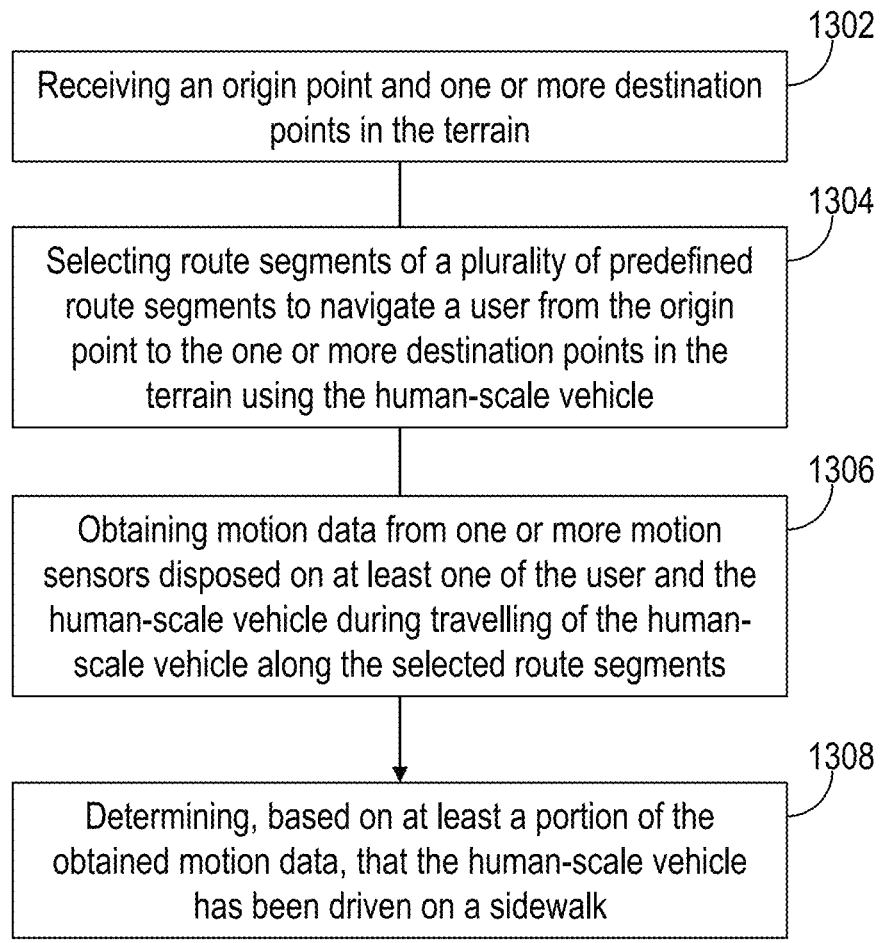
FIG. 13 is a flowchart of a method of determining that a human-scale vehicle has been driven on a sidewalk, according to some embodiments of the invention.

Reference is now made to FIG. 13, which is a flowchart of a method of determining that a human-scale vehicle has been driven on a sidewalk, according to some embodiments of the invention.

Some embodiments may include receiving 1302 an origin point and one or more destination points in the terrain (e.g., by computing device 710 as described above with respect to FIG. 7).

Some embodiments may include selecting 1304 route segments of a plurality of predefined route segments to navigate the user from the origin point to the one or more destination points in the terrain using the human-scale vehicle (e.g., by computing device 710 as described above with respect to FIG. 7).

Some embodiments may include obtaining 1306 motion data from one or more motion sensors during traveling of the human-scale vehicle along the selected route segments (e.g., as described above with respect to FIG. 7). The one or more motion sensors may include, for example, one or more accelerometers, one or more gyroscopes, etc. In some embodiments, the one or more motion sensors may be motion sensors of the computing device. In some embodiments, the one or more motion sensors may be wearable by the user of the human-scale vehicle. In some embodiments, the one or more motion sensors may be disposed on the human-scale vehicle. In some embodiments, the one or more motion sensors may be motion sensors of the human-scale vehicle.

Some embodiments may include determining 1308, based on at least a portion of the obtained motion data, that the human-scale vehicle has been driven on a sidewalk (e.g., by computing device 710 and/or by remote computing device 730 as described above with respect to FIGS. 7 and 11).

Some embodiments may include determining that the human-scale vehicle has been driven on the sidewalk further based on geolocation data from one or more geolocation sensors. The one or more geolocation sensors may be disposed on at least one of the user and the human-scale vehicle (e.g., as described above with respect to FIG. 7).

Some embodiments may include identifying locations in the terrain in which the human-scale vehicle has been driven on the sidewalk (e.g., as described above with respect to FIG. 7).

Some embodiments may include issuing a notification that the human-scale vehicle has been driven on the sidewalk (e.g., as described above with respect to FIG. 7). For example, the notification may be issued to the user (e.g., using the user interface, as described hereinabove) or to a third authorized party (e.g., municipal authority, etc.).

Figure 14:
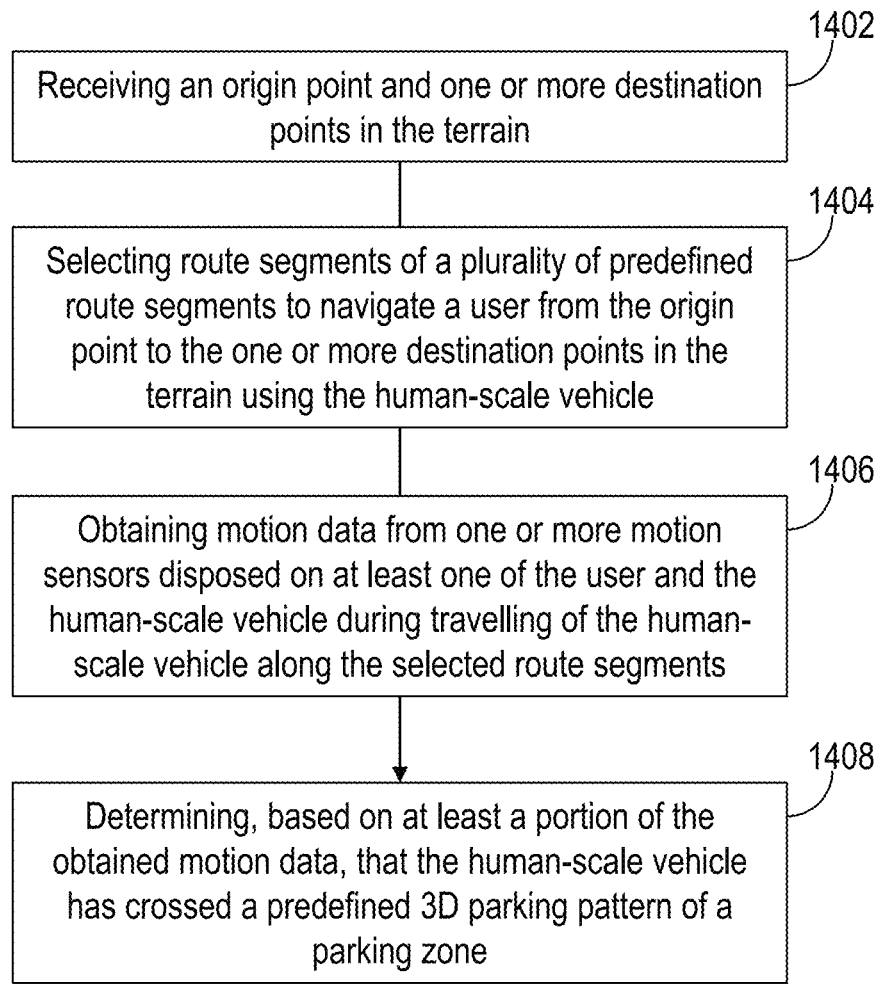
FIG. 14 is a flowchart of a method of determining that a human-scale vehicle has crossed a predefined three-dimensional (3D) parking pattern of a parking zone, according to some embodiments of the invention.

Reference is now made to FIG. 14, which is a flowchart of a method of determining that a human-scale vehicle has crossed a predefined three-dimensional (3D) parking pattern of a parking zone, according to some embodiments of the invention.

Some embodiments may include receiving 1402 an origin point and one or more destination points in the terrain (e.g., by computing device 710 as described above with respect to FIG. 7).

Some embodiments may include selecting 1404 route segments of a plurality of predefined route segments to navigate the user from the origin point to the one or more destination points in the terrain using the human-scale vehicle (e.g., by computing device 710 as described above with respect to FIG. 7).

Some embodiments may include obtaining 1406 motion data from one or more motion sensors during traveling of the human-scale vehicle along the selected route segments (e.g., as described above with respect to FIG. 7). The one or more motion sensors may include, for example, one or more accelerometers, one or more gyroscopes, etc. In some embodiments, the one or more motion sensors may be motion sensors of the computing device. In some embodiments, the one or more motion sensors may be wearable by the user of the human-scale vehicle. In some embodiments, the one or more motion sensors may be disposed on the human-scale vehicle. In some embodiments, the one or more motion sensors may be motion sensors of the human-scale vehicle.

Some embodiments may include determining 1408, based on at least a portion of the obtained motion data, that the human-scale vehicle has crossed a predefined 3D parking pattern of a parking zone (e.g., by computing device 710 as described above with respect to FIG. 7).

Some embodiments may include determining, based on at least a portion of the obtained motion data, that the human-scale vehicle has crossed the predefined 3D parking pattern of a parking zone, and further determining, based on geolocation data from one or more geolocation sensors that the human-scale vehicle is within the parking zone. Some embodiments may include preventing the user from locking the human-scale vehicle if the human-scale vehicle is not within the parking zone. For example, as described above with respect to FIG. 7.

Some embodiments may include determining, based on at least a portion of the obtained motion data, that the human-scale vehicle has crossed the predefined 3D parking pattern of a parking zone, and further determining, based on geolocation data from one or more geolocation sensors that the human-scale vehicle has left the parking zone. Some embodiments may include preventing the user from unlocking the human-scale vehicle if the human-scale vehicle is not within the parking zone. For example, as described above with respect to FIG. 7.

Advantageously, the disclosed system and method may navigate a user in a terrain (e.g., urban area and/or areas between two or more urban areas) through selected route segments that are most suitable for driving using human-scale vehicles. Such route segments may include, for example roadway sections, pavement sections, bicycle lane sections, crosswalks, underground crossings, overhead passages, passageways, etc. The route segments may be selected from a plurality of predefined route segments. The predefined route segments may be predefined based on analysis of a plurality of ride datasets received from users of human-scale vehicles. The route segments may be continuously updated based on, for example, motion data obtained by motion sensors of the user during the actual ride along the selected route segments. In this manner, the disclosed system and method may provide safer and faster navigation in the terrain using the human-scale vehicle as compared to current navigation systems and methods that typically treat human-scale vehicles as small automotive vehicles or pedestrians.

Aspects of the present invention are described above with reference to flowchart illustrations and/or portion diagrams of methods, apparatus (systems) and computer program products according to embodiments of the invention. It will be understood that each portion of the flowchart illustrations and/or portion diagrams, and combinations of portions in the flowchart illustrations and/or portion diagrams, can be implemented by computer program instructions. These computer program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or portion diagram or portions thereof.

These computer program instructions can also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or portion diagram portion or portions thereof. The computer program instructions can also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or portion diagram portion or portions thereof.

The aforementioned flowchart and diagrams illustrate the architecture, functionality, and operation of possible implementations of systems, methods and computer program products according to various embodiments of the present invention. In this regard, each portion in the flowchart or portion diagrams can represent a module, segment, or portion of code, which includes one or more executable instructions for implementing the specified logical function(s). It should also be noted that, in some alternative implementations, the functions noted in the portion can occur out of the order noted in the figures. For example, two portions shown in succession can, in fact, be executed substantially concurrently, or the portions can sometimes be executed in the reverse order, depending upon the functionality involved. It will also be noted that each portion of the portion diagrams and/or flowchart illustration, and combinations of portions in the portion diagrams and/or flowchart illustration, can be implemented by special purpose hardware-based systems that perform the specified functions or acts, or combinations of special purpose hardware and computer instructions.

In the above description, an embodiment is an example or implementation of the invention. The various appearances of "one embodiment", "an embodiment", "certain embodiments" or "some embodiments" do not necessarily all refer to the same embodiments. Although various features of the invention can be described in the context of a single embodiment, the features can also be provided separately or in any suitable combination. Conversely, although the invention can be described herein in the context of separate embodiments for clarity, the invention can also be implemented in a single embodiment. Certain embodiments of the invention can include features from different embodiments disclosed above, and certain embodiments can incorporate elements from other embodiments disclosed above. The disclosure of elements of the invention in the context of a specific embodiment is not to be taken as limiting their use in the specific embodiment alone. Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described. Meanings of technical and scientific terms used herein are to be commonly understood as by one of ordinary skill in the art to which the invention belongs, unless otherwise defined. While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

The invention claimed is:

1. A method of navigating through a terrain using a human-scale vehicle, the method comprising:
   receiving an origin point and one or more destination points in the terrain;
   selecting route segments of a plurality of predefined route segments to navigate a user from the origin point to the one or more destination points in the terrain using the human-scale vehicle;
   obtaining motion data from one or more motion sensors disposed on at least one of the user and the human-scale vehicle during traveling of the human-scale vehicle along the selected route segments;
   determining, based on at least a portion of the obtained motion data, terrain characteristics of the selected route segments;
   updating at least one ride database according to the terrain characteristics, the database comprising, for each of the plurality of the route segments, an entry pointing to one or more end points, wherein the updating comprising automatically partitioning at least one of the segments into two or more segments;
   updating the selection of one or more of the predefined route segments based on the at least one ride database;
   generating, on a display of a computing device, one or more notifications based on the selected route segments, the notifications indicative of one or more navigation instructions; and
   determining, based on at least a portion of the obtained motion data, that the human-scale vehicle has been driven on a sidewalk, or that the human-scale vehicle has crossed a predefined 3D parking pattern bordering a parking zone within the terrain.

2. The method of claim 1, wherein the updating of one or more of the predefined route segments is based on the terrain characteristics determined for the respective one or more selected route segments.

3. The method of claim 1, comprising identifying locations in the terrain in which the human-scale vehicle has been driven on the sidewalk.

4. The method of claim 1, comprising determining, based on geolocation data from one or more geolocation sensors disposed on at least one of the user and the human-scale vehicle that the human-scale vehicle is within the parking zone.

5. The method of claim 4, comprising preventing the user from locking the human-scale vehicle if the human-scale vehicle is not within the parking zone.

6. The method of claim 1, comprising determining, based on geolocation data from one or more geolocation sensors disposed on at least one of the user and the human-scale vehicle that the human-scale vehicle has left the parking zone.

7. The method of claim 6, comprising preventing the user from unlocking the human-scale vehicle if the human-scale vehicle is not within the parking zone.

8. The method of claim 1, comprising detecting one or more driving-related events based on at least a portion of the obtained motion data.

9. The method of claim 8, comprising updating the selection of the route segments based on the one or more detected driving-related events.

10. The method of claim 8, comprising updating one or more of the predefined route segments based on the one or more driving-related events detected in the respective one or more selected route segments.

11. A method of navigating through a terrain using a human-scale vehicle, the method comprising:
   receiving an origin point and one or more destination points in the terrain;
   selecting route segments of a plurality of predefined route segments to navigate a user from the origin point to the one or more destination points in the terrain using the human-scale vehicle;
   obtaining motion data from one or more motion sensors disposed on at least one of the user and the human-scale vehicle during traveling of the human-scale vehicle along the selected route segments;
   determining, based on at least a portion of the obtained motion data, terrain characteristics of the selected route segments;
   updating at least one ride database according to the terrain characteristics, the database comprising, for each of the plurality of the route segments, an entry pointing to one or more end points, wherein the updating comprising automatically partitioning at least one of the segments into two or more segments;
   updating the selection of one or more of the predefined route segments based on the at least one ride database and based on at least a portion of the obtained motion data;
   generating, on a display of a computing device, one or more notifications based on the selected route segments, the notifications indicative of one or more navigation instructions; and
   at least one of selecting the route segments, and updating the selection thereof based on known driving skills of the user of the human-scaled vehicle.

12. The method of claim 11, comprising updating the navigation instructions based on the determined terrain characteristics.

13. The method of claim 11, comprising at least one of generating and updating the navigation instructions based on known driving skills of the user.

14. A method of navigating through a terrain using a human-scale vehicle, the method comprising:
   receiving an origin point and one or more destination points in the terrain;
   selecting route segments of a plurality of predefined route segments to navigate a user from the origin point to the one or more destination points in the terrain using the human-scale vehicle;
   obtaining motion data from one or more motion sensors disposed on at least one of the user and the human-scale vehicle during traveling of the human-scale vehicle along the selected route segments;
   determining, based on at least a portion of the obtained motion data, terrain characteristics of the selected route segments;
   receiving a plurality of ride datasets for the user of the human-scale vehicle, each of the ride datasets comprises selected route segments and motion data obtained during traveling of the human-scale vehicle along the selected route segments;
   updating at least one of the ride datasets according to the terrain characteristics, the database comprising, for each of the plurality of the route segments, an entry pointing to one or more end points, wherein the updating comprising automatically partitioning at least one of the segments into two or more segments;
   determining driving patterns for the user based on at least a portion of the ride datasets;
   updating the selection of one or more of the predefined route segments based on the at least one ride dataset; and
   generating, on a display of a computing device, one or more notifications based on the selected route segments, the notifications indicative of one or more navigation instructions.

15. The method of claim 14, comprising:
   receiving a plurality of ride datasets for multiple users of human-scale vehicles, each of the ride datasets comprises selected route segments and motion data obtained during traveling of the human-scale vehicle along the selected route segments; and
   at least one of defining new route segments and updating the predefined route segments based on at least a portion of the ride datasets.

* * * * *